(12) United States Patent
McKean et al.

(10) Patent No.: US 11,234,669 B2
(45) Date of Patent: Feb. 1, 2022

(54) X-RAY IMAGING DEVICE

(71) Applicant: Adaptix Ltd, Oxfordshire (GB)

(72) Inventors: Wes McKean, Oxfordshire (GB); Steve Wells, Oxfordshire (GB); Gil Travish, Oxfordshire (GB)

(73) Assignee: Adaptix Ltd, Oxforshire (GB)

( * ) Notice: Subject to any disclaimer, the term of this patent is extended or adjusted under 35 U.S.C. 154(b) by 59 days.

(21) Appl. No.: 16/766,722

(22) PCT Filed: Nov. 23, 2018

(86) PCT No.: PCT/GB2018/053400
§ 371 (c)(1),
(2) Date: May 25, 2020

(87) PCT Pub. No.: WO2019/102216
PCT Pub. Date: May 31, 2019

(65) Prior Publication Data
US 2020/0383656 A1    Dec. 10, 2020

(30) Foreign Application Priority Data

Nov. 25, 2017    (GB) ...................................... 1719599

(51) Int. Cl.
| | |
|---|---|
| *A61B 6/00* | (2006.01) |
| *A61B 6/02* | (2006.01) |
| *A61B 6/06* | (2006.01) |
| *G21K 1/02* | (2006.01) |

(52) U.S. Cl.
CPC .............. *A61B 6/547* (2013.01); *A61B 6/025* (2013.01); *A61B 6/06* (2013.01); *A61B 6/4007* (2013.01); *A61B 6/4085* (2013.01); *A61B 6/4429* (2013.01); *G21K 1/025* (2013.01)

(58) Field of Classification Search
CPC ..... A61B 6/4007; A61B 6/4429; G21K 1/025
See application file for complete search history.

(56) References Cited

U.S. PATENT DOCUMENTS

| | | | |
|---|---|---|---|
| 2010/0189223 A1* | 7/2010 | Eaton ................... | H01J 35/065 378/68 |
| 2014/0177785 A1 | 6/2014 | Funk | |
| 2015/0320371 A1 | 11/2015 | Heath et al. | |

FOREIGN PATENT DOCUMENTS

| | | |
|---|---|---|
| WO | 2014/075699 A1 | 5/2014 |
| WO | 2017/185028 A1 | 10/2017 |

OTHER PUBLICATIONS

Patent Cooperation Treaty, International Search Report, PCT/GB2018/053400, dated Feb. 12, 2019.

(Continued)

*Primary Examiner* — Dani Fox
(74) *Attorney, Agent, or Firm* — Reichel Stohry Dean LLP; Mark C. Reichel; Natalie J. Dean

(57) ABSTRACT

An x-ray imaging device (10) comprising at least two substantially planar panels (20, 21), each panel comprising a plurality of x-ray emitters housed in a vacuum enclosure, wherein the at least two panels each have a central panel axis (28) and are arranged such that their central panel axes are non-parallel to one another, the device further comprising a panel retaining means and arranged such that the panel retaining means retains the at least two panels stationary in relation to an object during x-raying of the object.

20 Claims, 7 Drawing Sheets

(56) References Cited

OTHER PUBLICATIONS

Patent Cooperation Treaty, International Searching Authority, Written Opinion of the International Searching Authority, PCT/GB2018/053400, dated Feb. 12, 2019.

* cited by examiner

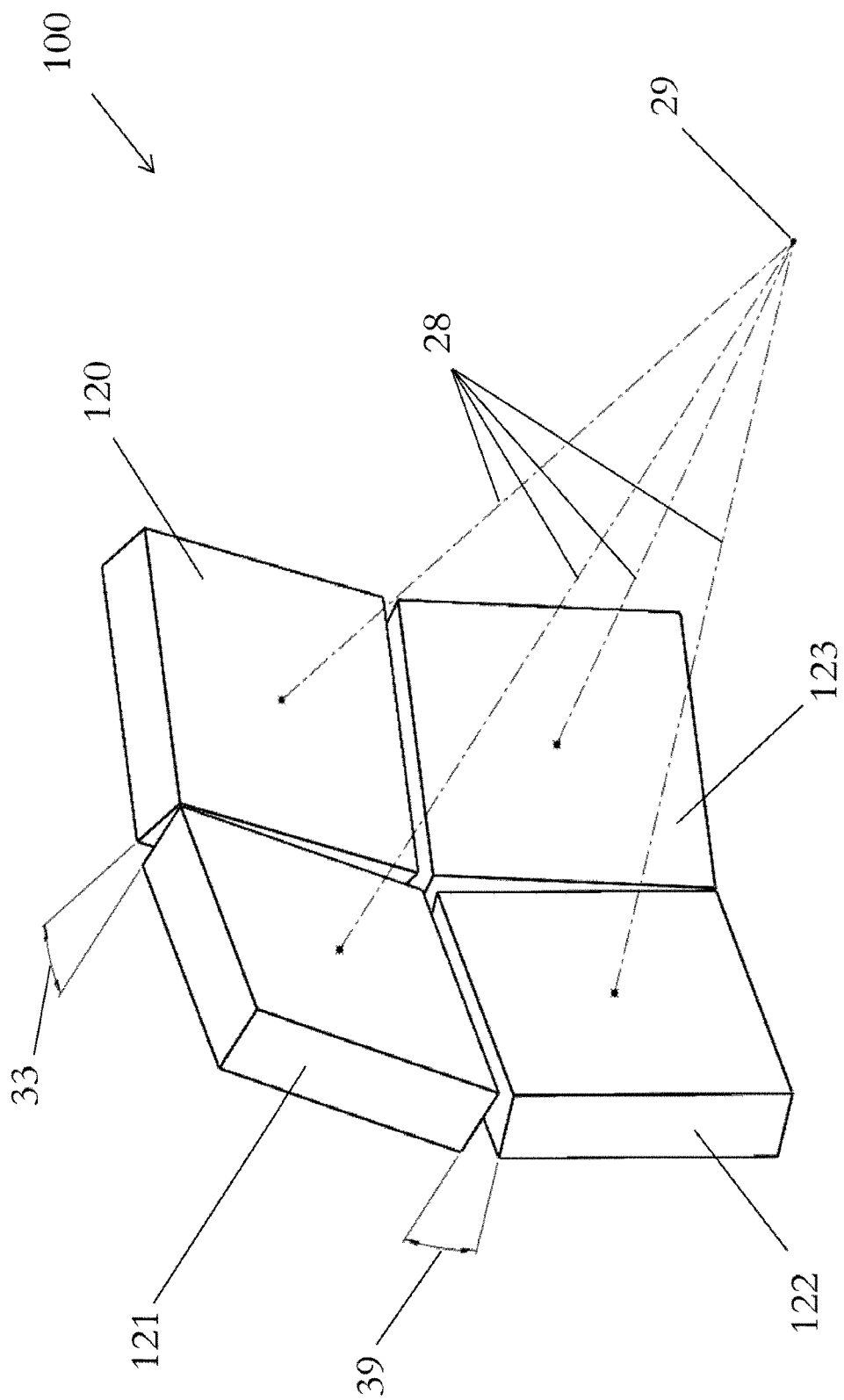

X-RAY IMAGING DEVICE

PRIORITY

The present application is related to, and claims the priority benefit of, and is a 35 U.S.C. 371 national stage application of, International Patent Application Serial No. PCT/GB2018/053400, filed Nov. 23, 2018, which is related to, and claims the priority benefit of, Great Britain Patent Application Serial No. 1719599.1, filed Nov. 25, 2017. The contents of each of these applications are hereby incorporated by reference in their entirety into this disclosure.

TECHNICAL FIELD

The present invention relates generally to an x-ray imaging device and a method of producing an x-ray image and finds particular, although not exclusive, utility in medicine.

BACKGROUND

This invention is concerned with x-ray sources and more specifically with multiple x-ray sources. It is well known that x-ray tubes can be moved in a controlled fashion using gantries and computer controlled motorized stages so as to image an object from multiple angles and positions. It is also known that multiple x-ray tubes can be arranged to accomplish similar tasks and with greater speed and precision, but with added cost and complexity.

It has also been disclosed that arrays of emitters can be constructed such that single linear or 2D configurations of emitters can cover multiple positions and angles for imaging. These "panels" are conceptually simple, offering a single vacuum enclosure which contains and supports all the emitters and targets of the distributed x-ray source.

Various other configurations have been considered in the literature, including groups of emitters built into multiple discrete units. In general, these configurations are selected based on general engineering considerations such as the mechanical fit.

Conventional x-ray systems rely on tubes to generate a cone of x-rays from a point source. These tube-based sources are relied on for substantially all medical x-ray imaging. As a consequence of the source geometry, the configurations possible for x-ray imaging systems are limited and generally include 2D "planar", 3D "CT" (computed tomography), and partially-3D "tomosynthesis" systems.

In the planar configurations, the source is positioned relative to the patient and detector either manually or with the assistance of a motorized gantry and then held in a single, fixed location with a single exposure being taken. These systems produce 2D shadowgrams, are generally inexpensive to deploy (low capital costs and low installation and maintenance costs), and are simple to operate at a low-cost per image. Planar imaging is lacking in a number of areas: quantification, indication specificity, ability to detect various anatomical anomalies, etc. Many of these deficiencies come from an inability to remove the impact (attenuation) of overlying and underlying tissue.

Computed Tomography (CT) systems rotate the source and detector about the object to be imaged (e.g. human body) and reconstruct a three-dimensional model of the object using tomography. CT generally addresses the deficiencies of planar imaging, however, at an order of magnitude increase in the cost of deployment, cost per use, dose to the patient, size, weight (and hence lack of portability), read time, etc. In critical care or serious conditions, the dose burden and costs are generally justified, but in more routine imaging or screening the risks and expenses are not always acceptable.

Digital Tomosynthesis (DT) systems typically move an x-ray source over a limited range of angles (positions) while pointing at the detector. While other configurations have been considered, conventional DT systems share the use of limit-angle coverage (e.g. 40°) and the use of different mathematical algorithms to reconstruct the partial-3D scene. DT generally offers a reasonable compromise between planar and CT. In some cases, DT can provide as accurate a clinical determination as CT, but at doses and costs much closer to those associated with planar imaging.

Because DT requires multiple exposures from a precisely movable and positioned source, these systems are installed in radiology suites, have relatively high deployment costs (compared to planar radiology) and are not mobile. The costs and complexity are largely a function of the (tube-based) source limitations.

The elimination of the need for movement is desirable. Such "distributed sources" have been considered in a number of configurations including the use of multiple conventional tubes positioned in an arc or a line; linear arrays of cathodes which can be individually activated; and, two-dimensional arrays of cold-cathodes. These fixed distributed sources eliminate the need to move the source and thereby can reduce the cost, complexity, and size requirements opening the opportunity for mobile 3D radiology. These types of sources can also increase the acquisition speed and thus reduce the likelihood of motion blur.

Distributed x-ray sources involve the optimization of several parameters beyond those already considered for single emitter sources (tubes) including coverage area, emitter pitch, topology (1D, 2D, square, triangle packing, etc.), emission angle, overall collimation, etc. In many applications, large coverage area is necessary or desirable. By example, for chest imaging in medicine (general radiology) an x-ray field of view of 40 cm×40 cm or more is desired. For such applications, a distributed array in a single housing may have to be large, say 50 cm×50 cm or more, and represent a significant volume and weight. Higher weights and volumes are often associated with higher costs. Moreover, there are engineering challenges with making vacuum enclosures which are simultaneously large, x-ray transmissive and do not excessively deflect under atmospheric pressure.

At the same time, the configuration of the x-ray emission from these large panels is not necessarily optimal for imaging. The angular coverage of an array is usually determined by the opening angle of the collimator. While it is possible to have each emitter at a different angle to the plane of the array, such configurations lead to very complex engineering and complex output patterns.

In general, the wider the coverage angle, the better the "slice resolution" (the minimum thickness in the 3D reconstruction that can be resolved), and the easier it is to identify objects that might otherwise be hidden by high attenuation objects (bones, amalgam, etc.). One approach to increasing the coverage angle of a distributed source is to shape the position and angle of the various emitters. In practice this sculpting of the source can most easily be done by introducing a bend-angle in what would otherwise be a planar arrangement of the emitters. This sculpting can be extended to creating an arc, however the benefits over a simple angle are limited because the detector remains a static plane.

There remains a desire to improve resolution and decrease dosage and cost.

BRIEF SUMMARY

Accordingly, in one aspect, the invention provides an x-ray imaging device comprising at least two substantially planar panels, each panel comprising a plurality of x-ray emitters housed in a vacuum enclosure, wherein the at least two panels each have a central panel axis and are arranged such that their central panel axes are non-parallel to one another, the device further comprising a panel retaining means and arranged such that the panel retaining means retains the at least two panels stationary in relation to an object during x-raying of the object.

A somewhat surprising result of this is that an incremental change in the angle of coverage can substantially improve the image reconstruction and slice resolution. While this effect can be difficult to quantify in general, in one simulation result a two-panel solution with 10-15° angle between the panel planes and 20° full-angle collimation per emitter resulted in reconstruction quality ("ground truth") substantially the same as that of the ideal emitter arrangement (along an arc).

In this respect, the x-ray emitters may be enclosed within a single vacuum enclosure in each panel. In one example, during use, it is expected that the panels, detector and subject remain stationary relative to one another.

The term planar is taken to mean that the x-ray emitters lie in a uniform plane, and the term central panel axis means an axis projecting normally to the plane of emitters in an approximately central position of the area of emitters.

It is important to distinguish between the full field of view coverage per emitter used in conventional distributed sources and those under consideration. In the sources used within the arrays described here each emitter covers only a portion of the field of view. This difference in geometry has implications for the use of multiple panels (an array of panels each panel having an array of x-ray emitters, possibly in a grid-like arrangement). For sources disclosed in the prior art including conventional moving tomosynthesis systems, the use of multiple arrays at angles to one another would require asymmetric collimation of each emitter and not necessarily provide an overall benefit. For the array of sources under consideration here with partial coverage per emitter, the angling of arrays relative to one another increases the relative angles while shaping the overall field of view.

A further benefit of the use of arrays of angled panels is the ability to better locate or determine the relative position of the source relative to the detector. In many clinical applications, for instance dental and in-bed imaging, the location of the detector is not well known as it is hidden (e.g. inside the mouth or behind the patient) and the relative position of the source can only be determined in software. The additional information provided by the increased and known angles between the panels aids in this position determination. Such position information further aids in the quality of the image reconstruction.

Another advantage of the use of arrays of angled panels is the lack of the requirement for any masking around the edges of the x-ray field.

Each x-ray emitter may emit x-rays in a conelet having a central conelet axis, and each of the at least two panels may be arranged such that the central conelet axes of each x-ray emitter in each respective panel are parallel to one another. Since the central panel axes of each panel are non-parallel this implies that the parallel central conelet axes of one panel are non-parallel to the parallel central conelet axes of an adjacent panel.

In this respect, the term conelet may mean a small cone and the term central conelet axis mean the axis projecting centrally through the cone of x-rays emitted from the emitter outlet.

An advantage of the panels having non-parallel central axes is a greater depth resolution of the object being x-rayed.

The x-ray imaging device may have two panels each with its central panel axis in a common plane, wherein each x-ray emitter may include a collimator having a common collimator angle and the two panels may be arranged such that the angle between their central panel axes may be approximately the same as the common collimator angle.

The term common collimator angle may determine the angle of the conelets and may lie in the range 10 to 50 degrees, or 18 to 45 degrees. The common collimator angle may be set during manufacture, or otherwise, dependent on the likely use for the device. For instance, human dental applications may have an angle of 35 to 45 degrees, whereas human chest applications may have an angle of 18 to 30 degrees. The common collimator angles also determine the size of the area of x-rays received at the detector and the presence or otherwise, and the degree, of overlap between adjacent emitters and panels. The common collimator angles used herein may be "full opening" angles.

The x-ray imaging device may have n panels, n being more than two, arranged side-by-side in a linear array each panel with its central panel axis lying in a common plane, wherein each x-ray emitter may include a collimator having a common collimator angle and the two outer panels of the array may be arranged such that the angle between their central panel axes may be approximately the same as the common collimator angle, and each intervening panel may be arranged such that the angle between its central panel axis and that of the adjacent panel may be calculated by the formula (the common collimator angle)/(n−1).

The x-ray imaging device may have an arrangement of four or more panels, arranged in two or more rows, each panel arranged such that their central panel axes converge on a common point distal from the device, wherein each x-ray emitter may include a collimator having a common collimator angle and the panels at the ends of each row may be arranged such that the angle between their central panel axes and a line connecting the common point to the centre of the arrangement of panels may be approximately the same as the common collimator angle.

The x-ray imaging device may have an arrangement of six or more panels, arranged in two or more rows, each panel in a first row may be arranged such that their central panel axes converge on a first common point distal from the device, and each panel in each subsequent row may be arranged such that their central panel axes converge on respective subsequent common points distal from the device, wherein each x-ray emitter may include a collimator having a common collimator angle and the panels at the ends of each row may be arranged such that the angle between their central panel axes and a line connecting the relevant common point to the centre of the arrangement of panels in that row may be approximately the same as the common collimator angle.

In some examples, the outer corner panels in any arrangement of panels, such as an arrangement of 3×3 panels, may be "angled-in" more towards the object with respect to the other panels in their respective row, or "angled-out" with respect to the other panels in their respective row to widen the area of x-rays, as required. accordingly, it is possible that more than one common point is created in each row, such that the two outer panels have the same common point which is different from the common point for any intervening panels in the same row.

The x-ray imaging device may have two panels arranged such that the angle between their central panel axes in each of two of the three cardinal axes lies in the range 1 to 89 degrees.

The angle between these two central panel axes in each of two of the three cardinal panel axes may lie in the range 5 to 45 degrees, or 10 to 20 degrees, or 10 to 45 degrees.

The x-ray imaging device may further comprise a digital x-ray detector having a central detector panel axis and a controller for controlling each x-ray emitter individually. In this regard, the detector may be planar and the term central detector panel axis may mean an axis projecting normally to the plane of the detector in an approximately central position of the planar detector area.

The x-ray imaging device may be arranged such that the distance between the panels and the detector is in the range of one to two times the thickness of the object to be x-rayed.

The x-ray imaging device may further comprise detector retaining means, and may be arranged such that the detector retaining means retains the detector stationary in relation to the object during x-raying of the object.

The x-ray imaging device may comprise between two and sixteen panels.

The x-ray imaging device may further comprise a processor for processing data produced by the detector, as a result of receiving x-rays, and for producing a subsequent image.

The processor may be configured to process data received over a period of time to produce a 3D tomosynthesis model of an x-rayed object wherein the received x-rays have been emitted by different emitters in the panels and have passed through the object in different directions.

The processor may be configured to determine the relative angle of the central panel axis of each panel relative to the central detector panel axis in two of the three cardinal axes.

The x-ray imaging device may further comprise positioning means for adjusting the position of at least one of the at least two panels relative to the other of the at least two panels, prior to x-raying of the object. Such positioning means are well understood and can include arms, clamps, brackets and the like in order to position each panel, or set of panels, relative to one another. In this regard, the relative position includes pitch, yaw and roll. In this way, once the panels have been moved to their desired position they remain static during the x-ray procedure. Alternatively, the panels may be manufactured such that they sit in a housing with pre-set relative positions.

An x-ray imaging device may be provided which includes more than one x-ray imaging device (with more than one detector) but having a shared processor to produce a 3D image. The x-ray imaging device may be known as an x-ray imaging system.

In a second aspect, the invention provides a method of producing an x-ray image of an object comprising the steps of providing an x-ray imaging device according to the first aspect; providing an object between the detector and the panels; causing x-rays to be emitted from the panels; processing data received by the detector as a result of receiving x-rays; and producing an image therefrom.

The method may further comprise the step of using the processor to determine the relative angle of the central panel axis of each panel relative to the central detector panel axis of the detector in two of the three cardinal axes so as to improve the accuracy of the produced image.

The method may further comprise the step of the detector receiving data over a period of time wherein the received x-rays have been emitted by different emitters in the panels and have passed through the object in different directions, and the processor processing said data to produce a 3D tomosynthesis model of the object.

The x-ray imaging device may include any of the features described in relation to the first aspect.

BRIEF DESCRIPTION OF THE DRAWINGS

The above and other characteristics, features and advantages of the present invention will become apparent from the following detailed description, taken in conjunction with the accompanying drawings, which illustrate, by way of example, the principles of the invention. This description is given for the sake of example only, without limiting the scope of the invention. The reference figures quoted below refer to the attached drawings.

FIG. 5 is a perspective view of the four panel array of FIGS. 3 and 4;

DETAILED DESCRIPTION

Figure 1:
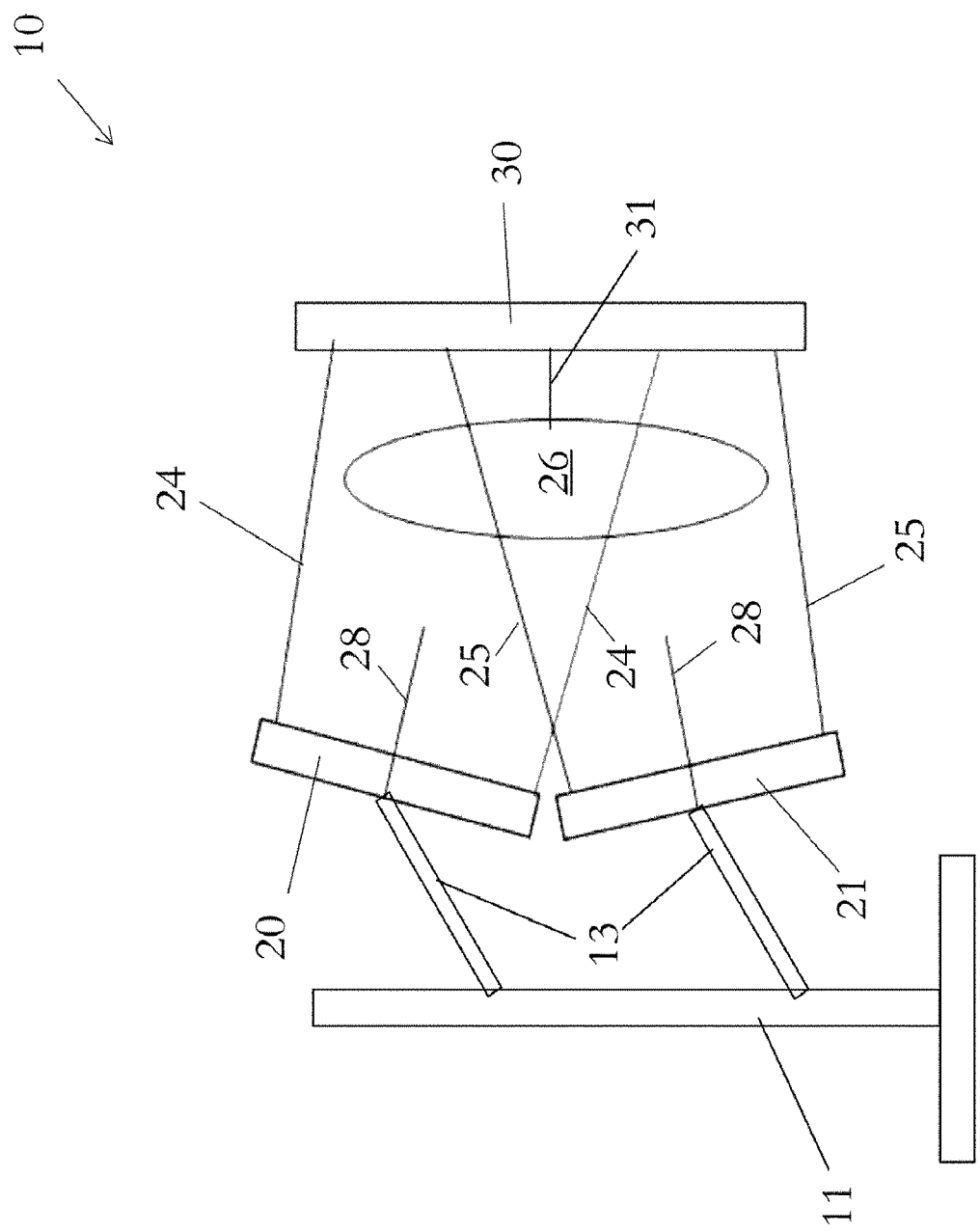
FIG. 1 is a schematic view of an x-ray imaging device.

The present invention will be described with respect to certain drawings but the invention is not limited thereto but only by the claims. The drawings described are only schematic and are non-limiting. Each drawing may not include all of the features of the invention and therefore should not necessarily be considered to be an embodiment of the invention. In the drawings, the size of some of the elements may be exaggerated and not drawn to scale for illustrative purposes. The dimensions and the relative dimensions do not correspond to actual reductions to practice of the invention.

Furthermore, the terms first, second, third and the like in the description and in the claims, are used for distinguishing between similar elements and not necessarily for describing a sequence, either temporally, spatially, in ranking or in any other manner. It is to be understood that the terms so used are interchangeable under appropriate circumstances and that operation is capable in other sequences than described or illustrated herein.

Moreover, the terms top, bottom, over, under and the like in the description and the claims are used for descriptive purposes and not necessarily for describing relative positions. It is to be understood that the terms so used are interchangeable under appropriate circumstances and that operation is capable in other orientations than described or illustrated herein.

It is to be noticed that the term "comprising", used in the claims, should not be interpreted as being restricted to the means listed thereafter; it does not exclude other elements or steps. It is thus to be interpreted as specifying the presence of the stated features, integers, steps or components as referred to, but does not preclude the presence or addition of one or more other features, integers, steps or components, or groups thereof. Thus, the scope of the expression "a device comprising means A and B" should not be limited to devices consisting only of components A and B. It means that with respect to the present invention, the only relevant components of the device are A and B.

Similarly, it is to be noticed that the term "connected", used in the description, should not be interpreted as being restricted to direct connections only. Thus, the scope of the expression "a device A connected to a device B" should not be limited to devices or systems wherein an output of device A is directly connected to an input of device B. It means that there exists a path between an output of A and an input of B which may be a path including other devices or means. "Connected" may mean that two or more elements are either in direct physical or electrical contact, or that two or more elements are not in direct contact with each other but yet still co-operate or interact with each other. For instance, wireless connectivity is contemplated.

Reference throughout this specification to "an embodiment" or "an aspect" means that a particular feature, structure or characteristic described in connection with the embodiment or aspect is included in at least one embodiment or aspect of the present invention. Thus, appearances of the phrases "in one embodiment", "in an embodiment", or "in an aspect" in various places throughout this specification are not necessarily all referring to the same embodiment or aspect, but may refer to different embodiments or aspects. Furthermore, the particular features, structures or characteristics of any embodiment or aspect of the invention may be combined in any suitable manner, as would be apparent to one of ordinary skill in the art from this disclosure, in one or more embodiments or aspects.

Similarly, it should be appreciated that in the description various features of the invention are sometimes grouped together in a single embodiment, figure, or description thereof for the purpose of streamlining the disclosure and aiding in the understanding of one or more of the various inventive aspects. This method of disclosure, however, is not to be interpreted as reflecting an intention that the claimed invention requires more features than are expressly recited in each claim. Moreover, the description of any individual drawing or aspect should not necessarily be considered to be an embodiment of the invention. Rather, as the following claims reflect, inventive aspects lie in fewer than all features of a single foregoing disclosed embodiment. Thus, the claims following the detailed description are hereby expressly incorporated into this detailed description, with each claim standing on its own as a separate embodiment of this invention.

Furthermore, while some embodiments described herein include some features included in other embodiments, combinations of features of different embodiments are meant to be within the scope of the invention, and form yet further embodiments, as will be understood by those skilled in the art. For example, in the following claims, any of the claimed embodiments can be used in any combination.

In the description provided herein, numerous specific details are set forth. However, it is understood that embodiments of the invention may be practised without these specific details. In other instances, well-known methods, structures and techniques have not been shown in detail in order not to obscure an understanding of this description.

In the discussion of the invention, unless stated to the contrary, the disclosure of alternative values for the upper or lower limit of the permitted range of a parameter, coupled with an indication that one of said values is more highly preferred than the other, is to be construed as an implied statement that each intermediate value of said parameter, lying between the more preferred and the less preferred of said alternatives, is itself preferred to said less preferred value and also to each value lying between said less preferred value and said intermediate value.

The use of the term "at least one" may mean only one in certain circumstances. The use of the term "any" may mean "all" and/or "each" in certain circumstances.

The principles of the invention will now be described by a detailed description of at least one drawing relating to exemplary features. It is clear that other arrangements can be configured according to the knowledge of persons skilled in the art without departing from the underlying concept or technical teaching, the invention being limited only by the terms of the appended claims.

In FIG. 1, the x-ray imaging device 10 includes two planar panels 20, 21 each comprising an array of x-ray emitters and collimators. The panels 20, 21 are held in place by arms 13 extending away from a support 11. It is understood, however, that these are merely examples, and other methods and structures may be used to hold the panels and detector(s) in place.

The panels' central panel axes are indicated by lines 28 projecting perpendicularly outwardly from the centre of the front surface of each panel. Each panel 20, 21 produces x-rays which emerge from the front faces of the panels. The outer limits of the x-ray envelope are shown by lines 24, 25. The x-rays are directed at the subject 26 and converge towards a detector 30 in the form of a panel located behind the subject, relative to the panels 20, 21. A central detector panel axis 31 is indicated by a line projecting perpendicularly outwardly from the centre of its front surface.

In this respect, the panels 20, 21 are emitter arrays, each packaged with its own cathode, anode and vacuum enclosure and powered either by a shared high voltage supply or by individual supplies to each emitter. The angle between the central panel axes 28 may be related to the opening angle of the collimators (common collimator angle) provided in the panels for collimating the produced x-rays. In one example, the angle between the central panel axes 28 is approximately the same as the opening angle of the collimators (the common collimator angle).

Figure 2:
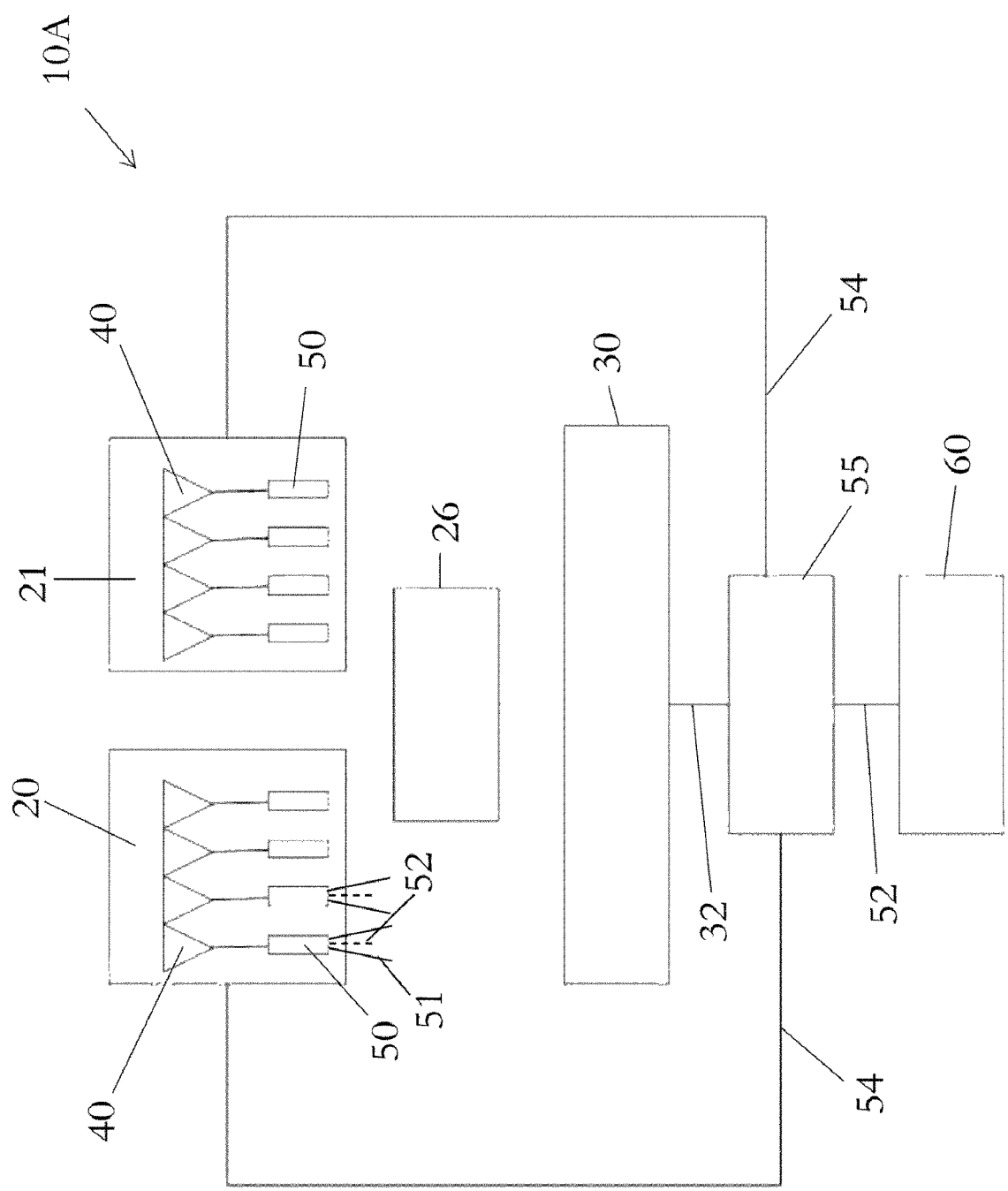
FIG. 2 is another schematic view of an x-ray imaging device.

In FIG. 2, the x-ray imaging device 10A comprises two panels 20, 21 shown by way of example with not-to-scale x-ray emitters 40 and collimators 50. The detector 30 is connected 32 to a controller 55 which in turn is connected 52 to a display 60. In use, x-rays are emitted from the collimators 50 in conelets 51 having central conelet axes 52. The signals received by the detector 30 are processed by either the controller 55 and/or the display 60 to produce an image on the display for review. The controller 55 is also connected 54 to the panels 20, 21 to thereby control the emission of x-rays. For instance, the controller can control which emitters are used to provide x-rays which emerge from the panels. It can control the synchronisation, sequencing and other characteristics of the emitted x-rays to produce defined areas and directions of x-rays for impinging on the subject 26. The controller may do this by controlling solenoids for selectively bending a path of electrons, produced by electron emitters, so that it either impinges on high energy x-ray producing material or onto absorbing (low energy x-ray producing) material. The controller is also connected to the detector 30 and so it is possible to manipulate the data defining which emitters are emitting x-rays with the received signals so that over time 3D images may be created.

Figure 4:
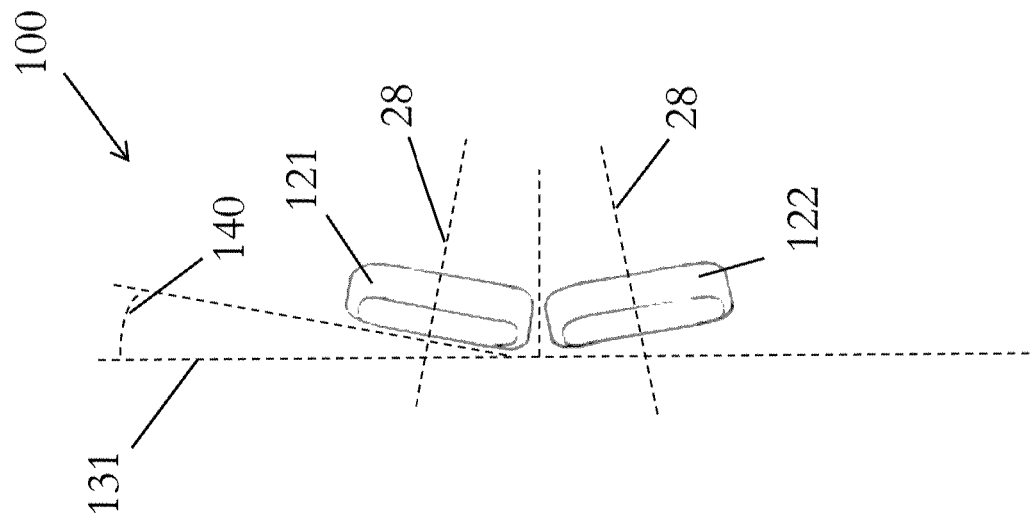
FIG. 4 is a side view of the four panel array of FIG. 3.
Figure 3:
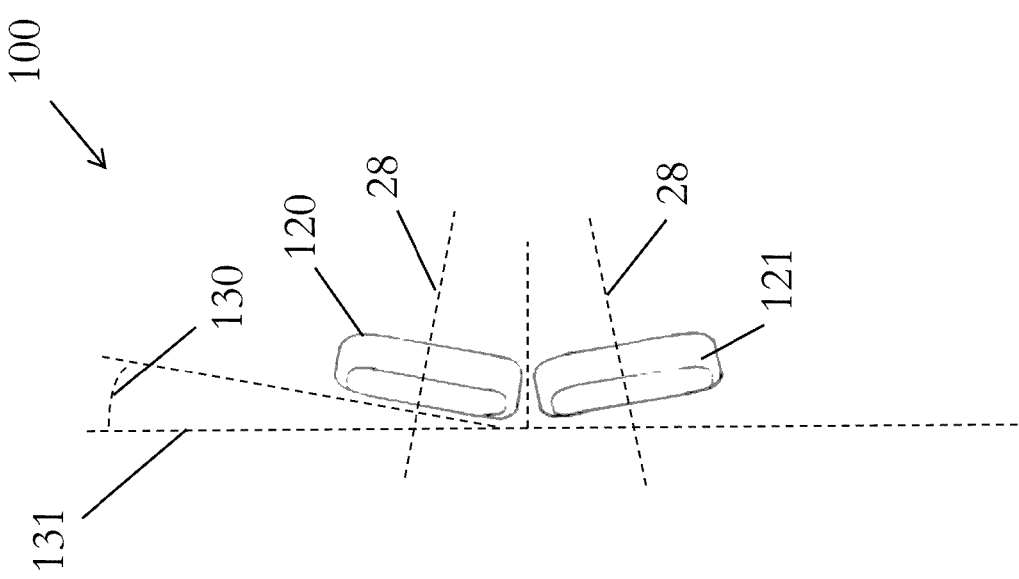
FIG. 3 is a plan view of the top two panels in a four panel array.

FIG. 3 shows a four panel source configured in a 2×2 array 100 from above. The panels are arranged to emit x-rays in an approximately horizontal direction. Each panel comprises a substantially rectangular block with a major plane forming the front surface from which the x-rays are emitted, in use. Only the top two panels 120, 121 are visible. Each panel has been rotated about a vertical axis by an angle 130 away from, and out of, a vertical "emitter" plane 131 so that the major plane of each panel is now not vertical. This angle 130 may be approximately half the common collimator angle. The panels have been angled inwards in this manner so that the angle between the front face of each panel is now less than 180 degrees. Also, each panel has been rotated about a horizontal axis which extends along the centre of the major plane of each panel from side to side. In this way the panels have been "angled-down". The angle through which they have been angled-down may also be approximately the same as the common collimator angle. The imaginary central panel axes 28 are shown to aid the understanding of the figure. FIG. 4, shows this angling-down more clearly as it shows the side view of the same 2×2 array 100 of FIG. 3. Here, one of the top panels 121 and one of the bottom panels 122 are shown. It can be seen that the bottom panel 122 has been angled upwardly and the top panel has been angled downwardly. The top panel 121 has been moved through an angle 140 away from the vertical "emitter" plane 131 about the horizontal axis described in relation to FIG. 3. This angle 140 may be approximately the same as the common collimator angle. By pointing the panels in this manner any x-rays emitted from the top two panels are directed below the horizontal and inwardly, and any emitted from the bottom two panels are directed above the horizontal and inwardly such that the x-rays from all four panels converge towards each other in the direction of the detector 30.

FIG. 5 shows a perspective view of the four panel array of FIGS. 3 and 4. It can be seen how the four panels 120, 121, 122, 123 are arranged in a 2×2 square pattern. The panels have been angled inwardly such that their central axes 28 all converge to a common single point 29. This common point 29 may lie on an imaginary line extending outwardly from the centre of the array 100 at a common angle to the plane of each of the four panels. However, in some circumstances the panels in the top row have a first common point and the panels in the second row have a second common point. It is possible that the first and second common points both lie on an imaginary line extending outwardly from the centre of the array 100 at a common angle to the plane of each of the four panels. The top panels 120, 121 have been angled in such that their front face planes are not in the same plane. The angle between those planes is shown by reference 33. The bottom two panels 122, 123 are oriented relative to each other in a similar manner. The bottom panels 122, 123 have also been angled in relative to the top two panels 120, 121 such that the angle between the front face planes of one top panel 121 and one bottom panel 122 is shown by reference 39. In one example, the angle 33 between the planes is approximately the same as the opening angle of the collimators (the common collimator angle).

In general, in tomosynthesis when detector and emitter planes are not parallel to one another, there results an "out of focus" image reconstruction. Therefore, it is important to know the spatial geometry of the imaging system prior to image reconstruction. Exact geometrical information is not always available due to the detector being masked by the subject. However, it is possible to recover and correct for emitter-detector spatial positions from attenuation data by employing methods of projective geometry.

For the robust determination of relative positions of the sources and detectors, it is necessary to compare images taken from different emitters. To aid this determination, a numerical mapping plane can be introduced in front of an emitter plane. This mapping plane may be parallel to the emitter plane. All stretching and deformations of images due to known tilts and rotations can be applied and the resulting corrected projections are placed on the centre of the mapping plane. When the geometry is known exactly the images have the same shape and size (assuming identical or at least known collimation angles). For "unknown" dislocations in the relative positions of the sources and detectors, the corresponding images will be mapped away from the centre of the mapping plane in a deterministic pattern. It is then possible to invert or deconvolve these patterns in order to determine the actual positions of the emitters relative to the detectors. For instance, due to magnification/demagnification effect, a tilt and/or rotation results in changes in area and shape of the imaged object taken from different emitters.

Numerical experiments have shown that such a technique is not particularly sensitive to small displacements and tilts. In other words, for common system geometries with single-plane emitters, the distortions on the mapping plane are not sufficiently amplified signals of the emitter position errors. Therefore, it can be difficult in practice to deconvolve the small distortions to accurately determine the true emitter locations. With multiple planes of emitters, however, additional information is available. The method described above can then be applied by extension to using multiple mapping planes. By suitable comparison of the different mapping planes, it is possible to have a more sensitive measure of the relative position errors.

The device may be pre-calibrated at the time of manufacture so that the relative orientation and positions of the emitters and detector are known. Alternatively, the device may be calibrated after manufacture. This may be necessary where the relative positions of one or more emitter panels and the detector have changed. The calibration may be undertaken by emitting x-rays from various emitters in a predetermined sequence, with no subject present, and identifying where they are received on the detector.

Figure 6:
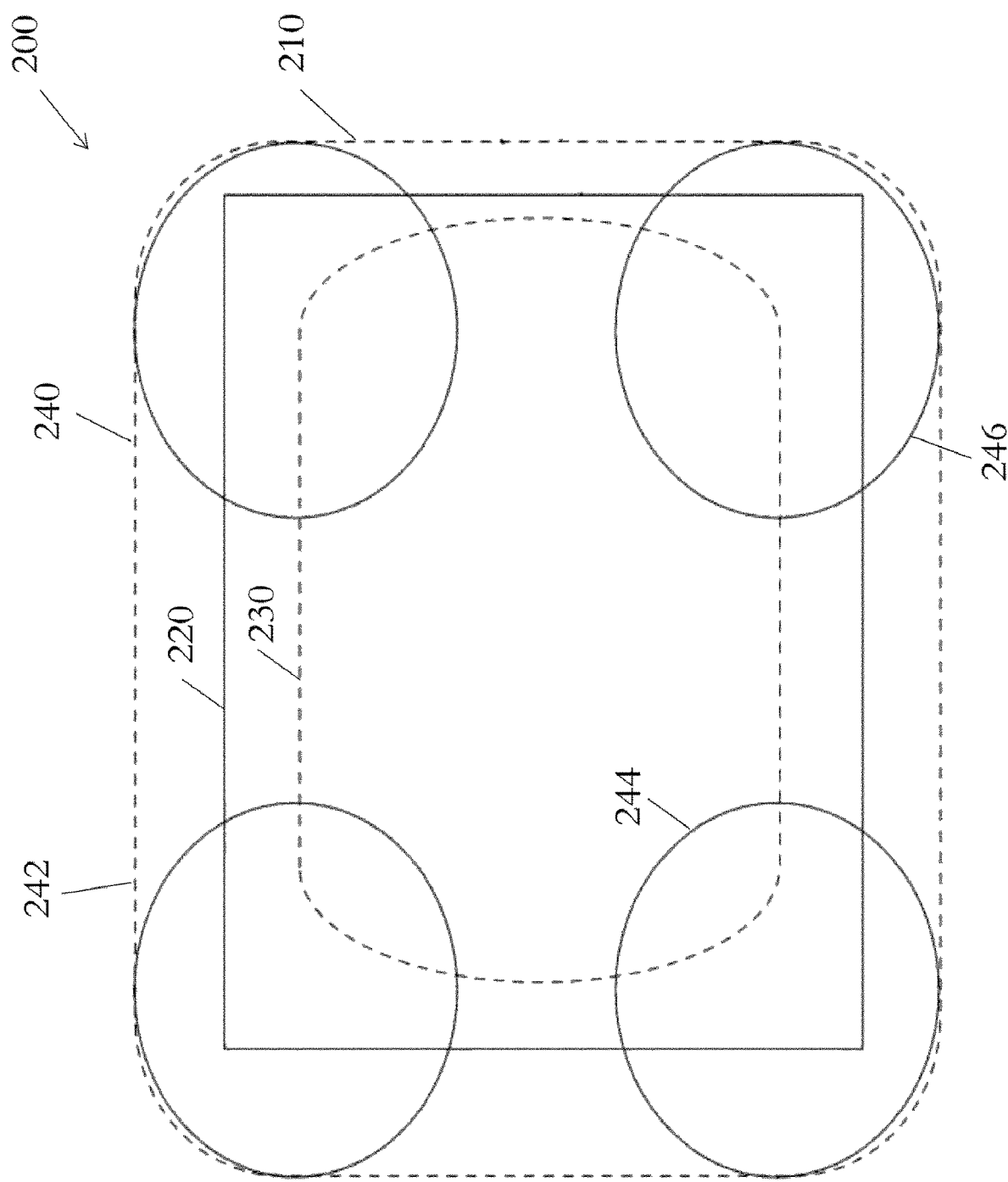
FIG. 6 is a schematic view of a detector plane view.

FIG. 6 shows a detector plane view 200 for a single panel emitter array and shows the active area of a detector 220 relative to a region of interest 230, and the outer envelope of the x-ray field 210. The relative positions and coverage areas of the x-ray cones produced from the four corner emitters in the array of emitters in the single panel are indicated as circles 240, 242, 244, 246, one in each corner of the envelope 210.

Figure 7:
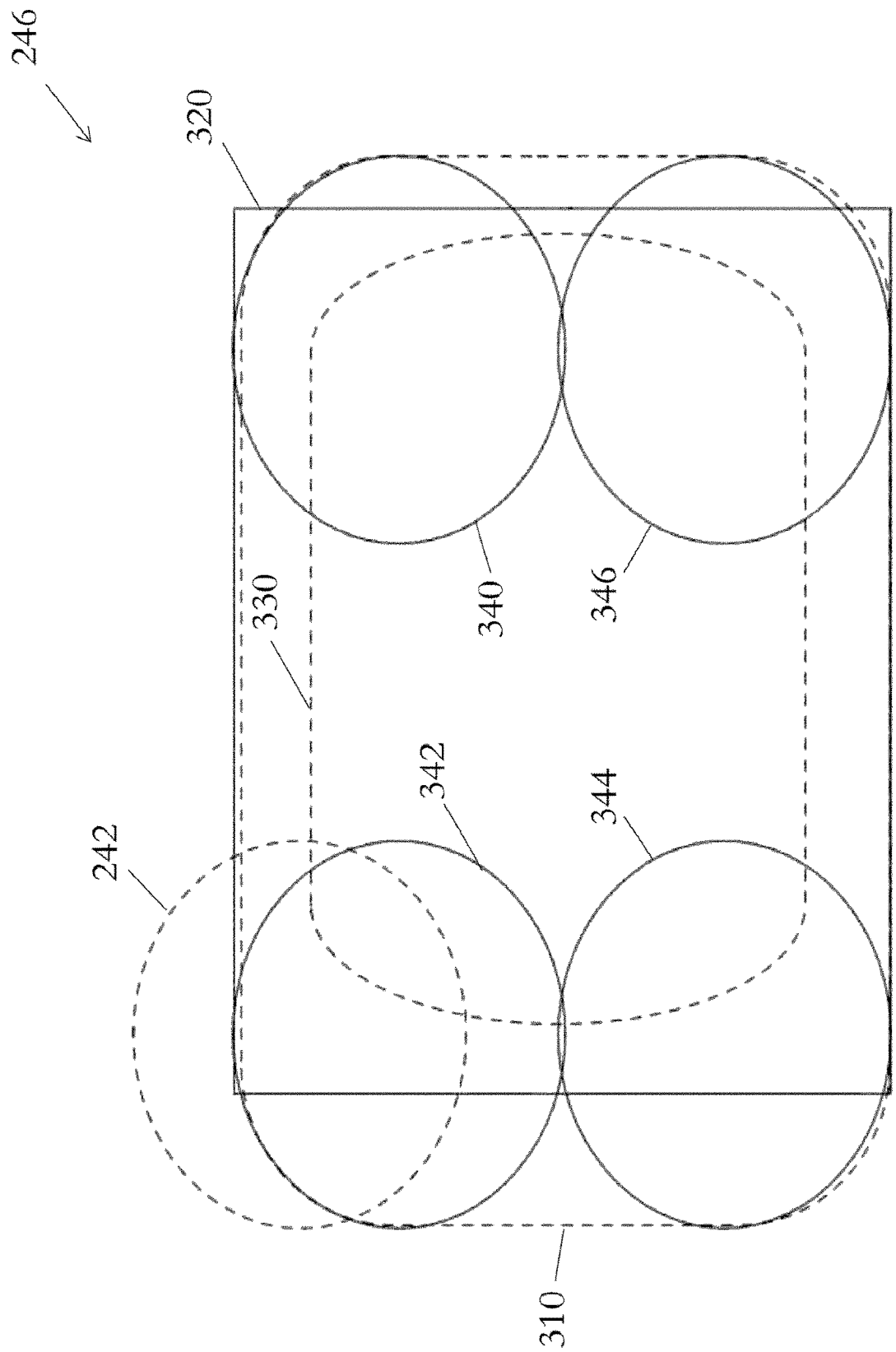
FIG. 7 is a schematic view of a different detector plane view.

By contrast, FIG. 7 shows a detector plane view for a two panel emitter array source set-up as shown in FIG. 1 where the two panels have been angled-in towards one another each about a horizontal axis passing through the centre of each panel from side to side. The active area of the detector 320 relative to a region of interest 330 is shown, as before, but the outer envelope of the x-ray field 310 has narrowed in the vertical plane. This is demonstrated by the relative positions and coverage areas of the x-rays from the upper two corner emitters of the top panel 20 and the lower two corner emitters from the bottom panel 21 being indicated as circles 340, 342, 344, 346, one in each corner of the envelope 310. The position of the x-ray cone from one of the corner emitters (242) from a single panel source (or two panel array which has the two panels having their major planes (front faces) parallel and in the same plane—i.e. not having been angled-in) is shown for reference. Relative to FIG. 5, the coverage area in one axis has moved in closer to the detector area, while still providing optimal angular coverage.

Figure 8:
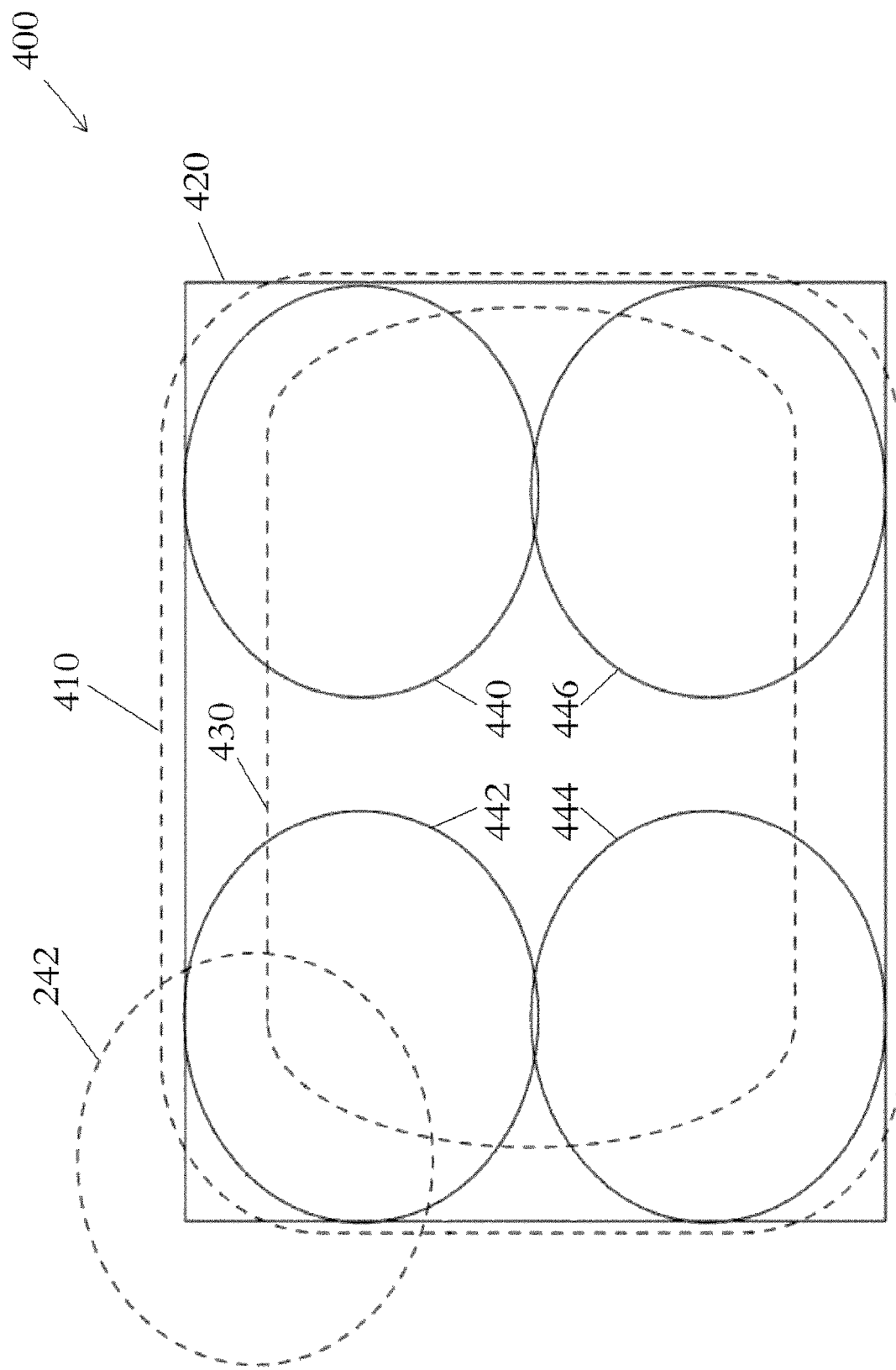
FIG. 8 is a schematic view of yet another different detector plane view.

FIG. 8 shows a detector plane view for a four panel emitter array source set-up as shown in FIGS. 3 to 5 where the two upper panels 120, 121 have been angled-down and inwardly towards one another, and the two lower panels 122 have been angled upwardly and inwardly towards one another so that the x-rays produced by the 4 panel device converge towards one another. The active area of the detector 420 relative to a region of interest 430 is shown, as before, but the outer envelope of the x-ray field 410 has narrowed in both the horizontal and the vertical plane. This is demonstrated by the relative positions and coverage areas of the x-rays from the upper outer corner of each of the upper two corner emitters of the top panels 120, 121 and the lower outer corner of each of the two corner emitters of the bottom panels 122 being indicated as circles 440, 442, 444, 446, one in each corner of the envelope 410. The position of the x-ray cone from one of the corner emitters (242) from a single panel source (or two or four panel array which has the two or four panels having their major planes (front faces) parallel and in the same plane—i.e. not having been angled-in) is shown for reference. Relative to FIGS. 6 and 7, the coverage area in both axes has moved in closer to the detector area, while still providing optimal angular coverage.

This effect reduces stray x-rays travelling beyond the detector, which is beneficial to operators. Furthermore, it removes the need for a mask to be used around the emitters and/or detector to safely absorb such stray and unwanted x-rays.

Although not shown it is to be understood that any number of panels may be employed in any regular, or irregular, pattern. For instance, a 6×2 array, a 3×3 array and so on. Some or all of the panels may be angled-in towards each other to converge the beam of x-rays so that a more focussed x-ray envelope may be produced.

The following table provides information on the possible conelet angles (common collimator angles) for various applications, together with the likely number of panels, the number of simultaneous conelets (i.e. the number of emitters firing simultaneously), and the ratio of conelet size (e.g. diameter or area) to detector size (e.g. width or length, or area) for a multi-panel array.

As can be seen, as the conelet angle reduces, the ratio of conelet size to detector size reduces. Therefore, the number of conelets required to image an object is increased. This allows greater control over what part of an object is struck by x-rays leading to greater optimisation of the process and less dosage. The contrasting angle from the multiple panels also allows for a greater depth of resolution.

In summary, the ratio of the conelet size to the detector size may be represented as 1/(no. of panels across+2)<ratio of the conelet size to the detector <0.7.

TABLE 1

| Application | Conelet angle | Number of panels | Number of simultaneous conelets | Ratio of conelet size to detector size in multi-panel cases |
|---|---|---|---|---|
| Dental | 35-45° | 1 | 1 | n/a |
| Ortho | 30-40° | 1, 1 × 2 | 1, possibly 2 | ~0.5-0.6 |
| Breast | 30-40° | 1, 1 × 2 | 1, possibly 2 | ~0.3 to 0.6 |
| Chest | 18-30° | 2 × 2, 3 × 3, 4 × 4 | 4 or 5 | ~0.2 to 0.4 |

The invention claimed is:

1. An x-ray imaging device comprising two substantially planar panels, each panel comprising a plurality of x-ray emitters housed in a vacuum enclosure, wherein the at least two panels each have a central panel axis and are arranged such that their central panel axes are non-parallel to one another, and are in a common plane, the at least two panels held stationary in relation to an object during x-raying of the object, wherein each x-ray emitter includes a collimator having a common collimator angle and the two panels are arranged such that the angle between their central panel axes is approximately the same as the common collimator angle.

2. The x-ray imaging device of claim 1, wherein each x-ray emitter emits x-rays in a conelet having a central conelet axis, and each of the at least two panels is arranged such that the central conelet axes of each x-ray emitter in each respective panel are parallel to one another.

3. The x-ray imaging device of claim 1, having n panels, n being more than two, arranged side-by-side in a linear array each with its central panel axis in a common plane, wherein each x-ray emitter includes a collimator having a common collimator angle and the two outer panels of the array are arranged such that the angle between their central panel axes is approximately the same as the common collimator angle, and each intervening panel is arranged such that the angle between its central panel axis and that of the adjacent panel is calculated by the formula (the common collimator angle)/(n−1).

4. The x-ray imaging device of claim 1, having an arrangement of four or more panels, arranged in two or more rows, each panel arranged such that their central panel axes converge on a common point distal from the device, wherein each x-ray emitter includes a collimator having a common collimator angle and the panels at the ends of each row are arranged such that the angle between their central panel axes and a line connecting the common point to the centre of the arrangement of panels is approximately the same as the common collimator angle.

5. The x-ray imaging device of claim 1, having an arrangement of six or more panels, arranged in two or more rows, each panel in a first row arranged such that their central panel axes converge on a first common point distal from the device, and each panel in each subsequent row arranged such that their central panel axes converge on respective subsequent common points distal from the device, wherein each x-ray emitter includes a collimator having a common collimator angle and the panels at the ends of each row are arranged such that the angle between their central panel axes and a line connecting the relevant common point to the centre of the arrangement of panels in that row is approximately the same as the common collimator angle.

6. The x-ray imaging device of claim 1, having two panels arranged such that the angle between their central panel axes in each of two of the three cardinal axes lies in the range 1 to 89 degrees.

7. The x-ray imaging device of claim 6, wherein the angle between their central panel axes in each of two of the three cardinal panel axes lies in the range 5 to 45 degrees.

8. The x-ray imaging device of claim 6, wherein the angle between their central panel axes in each of two of the three cardinal panel axes lies in the range 10 to 20 degrees.

9. The x-ray imaging device of claim 1, wherein the common collimator angle lies in the range 10 to 45 degrees.

10. The x-ray imaging device of claim 1, further comprising a digital x-ray detector having a central detector panel axis and a controller for controlling each x-ray emitter individually.

11. The x-ray imaging device of claim 10, arranged such that the distance between the panels and the detector is in the range of one to two times the thickness of the object to be x-rayed.

12. The x-ray imaging device of claim 10, wherein the detector is held stationary in relation to the object during x-raying of the object.

13. The x-ray imaging device of claim 1, comprising between two and sixteen panels.

14. The x-ray imaging device of claim 10, further comprising a processor for processing data produced by the detector, as a result of receiving x-rays, and for producing an image.

15. The x-ray imaging device of claim 14, wherein the processor is configured to process data received over a period of time to produce a 3D tomosynthesis model of an x-rayed object wherein the received x-rays have been emitted by different emitters in the panels and have passed through the object in different directions.

16. The x-ray imaging device of claim 14, wherein the processor is configured to determine the relative angle of the central panel axis of each panel relative to the central detector panel axis in two of the three cardinal axes.

17. The x-ray imaging device of claim 1, wherein the position of at least one of the at least two panels, relative to the other of the at least two panels, is adjustable prior to x-raying of the object.

18. A method of producing an x-ray image of an object comprising the steps of providing an x-ray imaging device, comprising two substantially planar panels, each panel comprising a plurality of x-ray emitters housed in a vacuum enclosure, wherein the at least two panels each have a central panel axis and are arranged such that their central panel axes are non-parallel to one another, and are in a common plane, the at least two panels held stationary in relation to an object during x-raying of the object, wherein each x-ray emitter includes a collimator having a common collimator angle and the two panels are arranged such that the angle between their central panel axes is approximately the same as the common collimator angle, the x-ray image device further comprising a digital x-ray detector having a central detector panel axis and a controller for controlling each x-ray emitter individually, the x-ray image device further comprising a processor for processing data produced by the detector, as a result of receiving x-rays, and for producing an image, wherein the processor is configured to process data received over a period of time to produce a 3D tomosynthesis model of an x-rayed object, wherein the received x-rays have been emitted by different emitters in the panels and have passed through the object in different directions;

providing an object between the detector and the panels;

causing x-rays to be emitted from the panels;

processing data received by the detector as a result of receiving x-rays; and producing an image therefrom.

19. A method of producing an x-ray image of an object according to claim 18, further comprising the step of:

using the processor to determine the relative angle of the central panel axis of each panel relative to the central detector panel axis of the detector in two of the three cardinal axes so as to improve the accuracy of the produced image.

20. The method of producing an x-ray image of an object according to claim 18, further comprising the step of:

the detector receiving data over a period of time wherein the received x-rays have been emitted by different emitters in the panels and have passed through the object in different directions; and the processor processing said data to produce a 3D tomosynthesis model of the object.

* * * * *